United States Patent [19]

Scharnberg

[11] Patent Number: 5,076,286
[45] Date of Patent: * Dec. 31, 1991

[54] DEFIBRILLATOR PAD ASSEMBLY AND METHOD FOR USING SAME

[75] Inventor: Lorne C. Scharnberg, West Des moines, Iowa

[73] Assignee: KAS Products, Inc., Des Moines, Iowa

[*] Notice: The portion of the term of this patent subsequent to Mar. 12, 2008 has been disclaimed.

[21] Appl. No.: 548,278

[22] Filed: Jul. 2, 1990

Related U.S. Application Data

[63] Continuation-in-part of Ser. No. 456,497, Dec. 26, 1989, Pat. No. 4,998,536.

[51] Int. Cl.⁵ .............................................. A61N 1/04
[52] U.S. Cl. .................... 128/800; 128/798; 128/802
[58] Field of Search ............... 128/798, 800, 802, 803; 606/32

[56] References Cited

U.S. PATENT DOCUMENTS

| | | | |
|---|---|---|---|
| 3,685,645 | 8/1972 | Kawaguchi | 206/63.2 R |
| 3,702,613 | 11/1972 | Panico et al. | 128/417 |
| 3,961,623 | 6/1976 | Milani et al. | 128/2.06 |
| 4,239,046 | 12/1980 | Ong | 128/640 |
| 4,267,840 | 5/1981 | Lazar et al. | 128/303.13 |
| 4,387,714 | 6/1983 | Geddes et al. | 128/303.13 |
| 4,458,696 | 7/1984 | Larimore | 128/798 |
| 4,524,087 | 6/1985 | Engel | 427/2 |
| 4,633,879 | 1/1987 | Ong | 128/641 |
| 4,748,983 | 6/1988 | Shigeta et al. | 128/639 |
| 4,779,630 | 10/1988 | Scharnberg et al. | 128/783 |
| 4,974,917 | 12/1990 | Kornerup | 128/798 |
| 4,998,536 | 3/1991 | Scharnberg | 128/800 |

FOREIGN PATENT DOCUMENTS 1115351 12/1981 Canada ................................. 128/798

*Primary Examiner*—Lee S. Cohen
*Attorney, Agent, or Firm*—Zarley, McKee, Thomte, Voorhees & Sease

[57] ABSTRACT

The defibrillator pad of the present invention comprises a lower layer of electrically conductive, tacky polymer and an upper layer of tin foil. The tin foil has apertures therein which expose portions of the upper surface of the polymer, thereby providing a nonskid surface for the electrode of the defibrillator paddles.

11 Claims, 1 Drawing Sheet

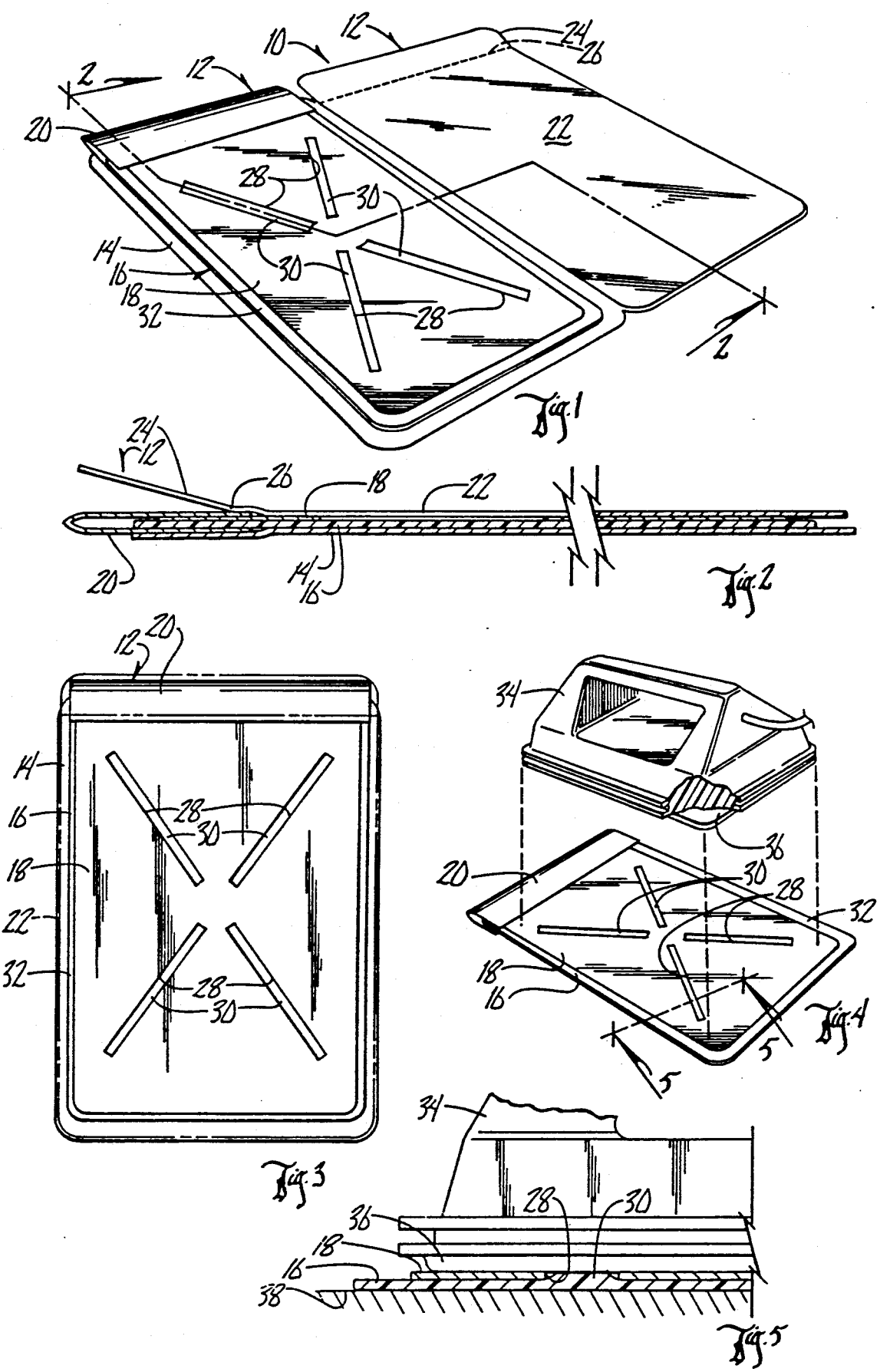

DEFIBRILLATOR PAD ASSEMBLY AND METHOD FOR USING SAME

This is a continuation-in-part of co-pending application Ser. No. 456,497, filed Dec. 26, 1989, now U.S. Pat. No. 4,998,536. This invention relates to a defibrillator pad assembly and a method for using same.

BACKGROUND OF THE INVENTION

Defibrillation is a process used for patients encountering fibrillation of the heart. The defibrillation process involves placing two electrode paddles on the patient's chest and applying a high density, electrical current to the patient so as to stimulate the heart and correct the fibrillation of the heart.

Dry skin on a patient causes the interface between the metal defibrillator paddles and the skin to have a high impedance. This can cause severe skin burns and may cause a significant reduction in the current delivered to the heart so as to prevent successful defibrillation.

Present methods for applying the defibrillator paddles to the skin involve the use of electrically conductive gels which are applied to the patient's skin and which are also applied to the defibrillator paddles. Often the gel is incompletely applied, leaving bare spots between the paddle and the patient's skin. These bare spots may result in burning of the patient's skin during discharge. Also, it is necessary for the user of the paddles to continue to apply pressure between the paddle and the patient's skin in order to insure a positive electrical contact therebetween.

Another disadvantage of presently used gels is that they are messy. Also, the gel often gets on the user's hands and arms, making it difficult for the user to perform other functions such as cardiopulmonary resuscitation.

Another presently used method for defibrillating involves the use of moisturized polymer pads which are enclosed within an airtight envelope The pads are removed from the envelope and placed on the patient's chest immediately prior to use. Then the defibrillator paddles are placed over the pads in preparation for their use. The disadvantage of these moisturized pads is that they tend to harden and become brittle after prolonged exposure to the atmosphere. Furthermore, they do not provide a strong adhesive bond between the pad and the patient's chest, and therefore, they sometimes slip or move after use.

Another method for defibrillating involves the use of a pad such as disclosed in U.S. Pat. No. 4,779,630. The method disclosed in this patent shows a polymer pad which is tacky and adhesive in its characteristics. It is also a good electrical conductor. The polymer pad is placed over the electrode on the defibrillator paddle. Then the paddle with the polymer pad attached thereto is placed over the patient's chest. The tackiness of the polymer pad causes the defibrillator paddle to adhere to the pad and also causes the polymer pad to adhere to the patient's chest, thereby providing a good electrical contact between the paddle and the chest. However, removal of the defibrillator paddle from the pad is difficult because the paddle is in complete direct contact with the tacky upper surface of the polymer pad.

Therefore, a primary object of the present invention is the provision of an improved defibrillator pad assembly and method for using same.

A further object of the present invention is the provision of a defibrillator pad assembly which utilizes conductive pads having a tacky under surface, but having an upper surface which is substantially less tacky so that the defibrillator paddles can be easily removed from the pad.

A further object of the present invention is a provision of an improved defibrillator pad assembly which utilizes pads which can be quickly adhered to the patient's chest and left there for a period of time during transporting of the patient.

A further object of the present invention is the provision of an improved defibrillator pad having an adhesive electrically conductive polymer on its lower surface, and having a layer of metal foil on its upper surface, the metal foil having apertures therein which expose portions of the upper surface of the conductive polymer.

A further object of the present invention is the provision of an improved defibrillator pad assembly and method for using same which is economical, efficient in operation, and inexpensive.

SUMMARY OF THE INVENTION

The present invention utilizes a laminated pad comprising a conductive polymer layer and a conductive metal foil layer. The polymer layer is on the bottom of the pad and is preferably a conductive polymer which can be purchased from Promeon division of Medtronic, Inc., 6951 Central Avenue, N.E., Minneapolis, Minnesota 55440, under the product designation RG 63 A, or RG 63 B, the latter being the preferred polymer. The conductive polymer includes thin fibers of polyethylene scrim which run through the polymer and which give the polymer sheet members strength. The scrim may also be made of other materials such as carbon, nickel-coated carbon, or other materials.

The conductive pad is shaped to fit the metal electrodes of the paddle, or it can be slightly larger than the electrodes of the paddles. The conductive pad has a strong tacky consistency which causes it to adhere to the patient's skin. The foil over the top surface of the conductive pad shields the defibrillator paddles from most of the tacky surface of the polymer pad However, the apertures within the foil sheet member expose at least portions of the tacky, upper surface of the polymer pad. Thus, the defibrillator paddle engages these exposed tacky portions of the polymer pad, and the paddle is thus adhered to the conductive pad. However, the force with which the defibrillator paddle is adhered to the conductive pad is less than the force with which the conductive pad adheres to the patient's skin.

Thus, it is possible, after the pad has been placed on the patient's chest to place the defibrillator paddles on the top of the pad, and to remove the defibrillator paddles without the pad being removed from the patient's skin.

Normally, the defibrillator pad of the present invention is stored between a bottom release liner and a top release liner to maintain the adhesiveness of the pad and to prevent dirt or other materials from adhering to the pad. The release liners are each treated with a silicone film which permits them to be separated easily from the tacky polymer of the defibrillator pad. When it is desired to use the pad, the top release liners are removed from the pad, and the pad itself is removed from the bottom release liner. The pad is then placed on the patient's chest with the polymer facing down so as to cause the pad to adhere to the patient's chest. The tackiness of the polymer will cause the pad to remain on the patient's chest without further aid from the operator. The operator then takes the defibrillator paddle and places the electrode of the defibrillator paddle downwardly on the upwardly presented surface of the foil sheet member of the defibrillator pad. Electrical continuity is provided between the defibrillator electrode and the patient's chest by virtue of the laminated structure of the metal foil and the polymer pad which comprise the defibrillator pad.

After the defibrillator paddle has been used to provide an electrical shock to the patient, the paddle can be removed easily due to the minimal tackiness which is presented by the portions of the upper surface of the polymer pad which are exposed through the apertures in the metal foil. This minimal tackiness prevents the paddles from sliding laterally on the metal foil during use. However, the tackiness is slight enough to permit removal of the paddles after the paddles have been used without causing the polymer pad to become detached from the patient's skin.

The defibrillator pads can be left on the patient's skin during transporting to the hospital so that they will be in place in the event a second defibrillation operation is required.

BRIEF DESCRIPTION OF THE DRAWINGS

FIG. 1 is a perspective view of a package containing two of the defibrillator pads of the present invention.

FIG. 2 is a sectional view taken along line 2—2 of FIG. 1.

FIG. 3 is a plan view of the defibrillator pad.

FIG. 4 is an exploded perspective view showing the manner in which a defibrillator paddle is applied to the pad.

FIG. 5 is a partial, sectional view showing the pad applied to a patient's skin and the defibrillator paddle applied to the pad.

DESCRIPTION OF THE PREFERRED EMBODIMENT

Referring to the drawings, the numeral 10 generally designates a package containing two defibrillator pad assemblies 12. Each pad assembly 12 includes a bottom release liner 14, a polymer pad 16, a metal foil sheet member 18, and an upper release liner 22. Bottom release liner 14 is made of paper which has been treated with a silicone film so that it can be easily removed from the polymer sheet member 16. Sheet member 16 is a conductive polymer purchased from Promeon, division of Medtronic, Inc., 8299 Central Avenue, N.E., Minneapolis, Minnesota 55432, under the product designation RG 63 A, or RG 63 B. The conductive polymer includes thin fibers of polyethylene scrim which run through the polymer and which give the polymer sheets strength. The scrim may also be made of other materials such as carbon, nickel-coated carbon, or other materials. The polymer is electrically conductive, and has a tacky consistency which causes it to adhere to any materials which it engages.

Adhered to the top surface of polymer sheet member 16 is conductive sheet member 18 which is preferably made of a metal foil. A paper gripping strip 20 is attached to one edge of the laminated foil sheet member 18 and polymer sheet member 16. This permits the operator to grasp the pad assembly 12 and separate the polymer sheet member and foil sheet member from the release liner 14. An upper release liner 22 is attached over the top surface of metal foil sheet member 18 to provide protection thereto during storage. The upper release liner 22 includes a folded gripping edge 24 which is folded along a folding line 26. Gripping edge 24 can be grasped by the operator to enable the operator to peel the upper release liner 22 from the upper surface of foil sheet 18. Upper release liner is also treated with a silicone coating to facilitate its easy removal.

Foil sheet 18 includes a plurality of apertures 28 therein which expose portions 30 of the polymer layer therebelow. The apertures 28 are shown to be elongated and rectangular in shape, with their longitudinal axes forming an x-shaped configuration. Other shapes and patterns of apertures can be used without detracting from the invention.

Also, the metal foil sheet member 18 is slightly smaller than the polymer sheet member 16 so as to leave an exposed parametric edge or border 32 of the polymer sheet member.

A conventional defibrillator paddle 34 is shown to include a rectangular electrode plate 36. As can be seen in FIG. 4, the electrode plate 36 is registered over the metal sheet member 18. It is then placed in contact with the metal sheet member 18 as is shown in FIG. 5.

In operation of the device, the person desiring to defibrillate a patient, removes the upper release liner 22, and then grasps the paper-gripping strip 20 and removes the polymer pad 16 and the metal foil 18 from the bottom release liner 14. The operator then places the pad assembly 12 on the patient's chest with the bottom surface of the polymer layer 16 in engagement with the patient's chest. The tacky nature of the polymer layer 16 causes it to adhere tightly to the patient's chest. The defibrillator paddle 34 is then placed on top of the metal foil member 18. As can be seen in FIG. 5, the electrode plate 36 engages and adheres to the exposed portions 30 of the polymer layer 16 through the apertures 28 in the foil sheet member 18. This causes the electrode plate 36 to adhere slightly to the pad 12 and creates a nonslip interface between the two. Also, facilitating this nonslip interface is the tacky surface provided by exposed polymer border 32 which surrounds the foil sheet member 18.

The preferred metal for the foil sheet member 18 is tin, but other types of metal foil can be used without detracting from the invention. Because of the partial exposure of the adhesive tacky polymer through the openings 28 and around the border 32, a nonskid surface is provided for the defibrillator paddle when it is placed against the defibrillator pad 12. There is also good electrical continuity between the electrode plate 36 and the skin of the patient so as to provide a stable clear tracing for an EKG (electrocardiogram) signal which can be read through the paddles in some applications. This helps the user of the paddles to monitor the patient's condition.

The exposed adhesive border around the outside perimeter of the pad also helps to minimize arcing which might occur between the edge of the metallic surface of the sheet member 18 and the patient's skin. It also provides an adhesive border to prevent the defibrillator electrode 36 from slipping off of the top of the defibrillator pad 12.

The defibrillator paddle 34, when used with the defibrillator pad 12 of the present invention, can be removed from the patient after defibrillation is complete. When it is lifted upwardly from the metal foil surface 18, the adhesive force between electrode 36 and the exposed portions 30 of pad 12 is substantially less than the adhesive force between the bottom surface of the polymer layer 16 and the patient's skin. Thus, it is possible to lift paddle 34 upwardly from the pad 12 without causing pad 12 to be detached from the patient's skin.

The pad 12 can stay in place on the patient and can be kept in place until the danger of further fibrillation has passed. If defibrillation is needed a second time, all that is necessary is to replace the paddles on the foil sheet members 18 and repeat the defibrillation process.

The present invention provides the important features of repeatability and dependability. The defibrillation process can be repeated numerous times with equally good results due to the good electrical contact which is obtained through the metal foil 18 and the polymer 16. Furthermore, the device is dependable in that because of good electrical contact being made, the defibrillation process occurs without burning or damaging the patient.

I claim:

1. A method for preparing a patient's chest having skin surface for accepting a defibrillator paddle, said method comprising:
    taking a laminated defibrillator pad having a bottom layer of electrically conductive polymer which is tacky so as to adhere to most surfaces it contacts, said pad having an upper layer comprising a sheet of electrically conductive material, said sheet having a plurality of apertures therein and being adhered to and in electrical contact with said bottom layer, portions of said bottom layer being exposed through said apertures in said sheet;
    placing said pad on said patient's chest with said bottom layer in contact with said skin surface of said patient's chest whereby said tackiness of said bottom layer will cause said pad to be detachably adhered to and in electrical contact with said skin surface of said patient's chest; and
    placing said defibrillator paddle in facing engagement with and electrical contact with said upper layer of said pad, whereby said exposed portions of said bottom layer are in contact with said paddle through said apertures in said upper layer and cause said paddle to be adhered to said pad with an adhering force which is less than the adhering force between said bottom layer and said patient's skin.

2. A method according to claim 1 and further comprising removing said defibrillator paddle from electrical contact with said upper layer of said pad, said upper layer at least partially shielding said defibrillator paddle from said tackiness of said bottom layer, whereby said pad will remain adhered to said skin surface of said patient's chest after removal of said defibrillator paddle from said upper layer of said pad.

3. A method according to claim 2 and further comprising forming said upper layer of said defibrillator pad from a metal foil material.

4. A defibrillator pad adapted to receive a defibrillator paddle comprising:
    a bottom layer of sheet material comprised of a conductive polymer having the characteristic of being tacky so as to detachably adhere to most surfaces it contacts, said bottom layer having an upper surface and a lower surface;
    an upper layer of metal foil having an upper surface and a lower surface, said upper layer having at least one aperture therein;
    said upper layer being superimposed over said bottom layer with said lower surface of said upper lower in electrical contact with and adhering to said upper surface of said bottom layer;
    said upper layer having perimetric edges and said bottom layer having perimetric edges which extend outwardly beyond said perimetric edges of said upper layer so as to expose a strip of said upper surface of said bottom layer extending completely around said perimetric edges of said upper layer; and
    portions of said upper surface of said tacky bottom layer being exposed through said aperture in said upper layer and around said perimetric edges of said upper layer so as to engage and adhere to said defibrillator paddle when said defibrillator paddle is placed in contact with said upper surface of said upper layer.

5. A defibrillator pad according to claim 4 wherein a plurality of said apertures are in said upper layer.

6. A defibrillator pad according to claim 5 wherein each of said aperture is elongated and has a longitudinal axis, said longitudinal axes of said apertures being arranged in an x-shaped pattern.

7. A defibrillator pad adapted to receive an electrode plate of a defibrillator paddle comprising:
    a bottom sheet member comprised of a conductive polymer having a tacky characteristic so as to detachably adhere to most surfaces it contacts, said bottom sheet member having an upper surface and a lower surface;
    an upper sheet member comprised of electrically conductive material and having an upper surface and a lower surface;
    said lower surface of said upper sheet member being in contact with and covering a first portion of said upper surface of said bottom sheet member and being adhered thereto by means of said tacky characteristic of said conductive polymer;
    said upper sheet member being shaped to expose at least one uncovered portion of said upper surface of said bottom sheet member so that when said electrode plate of said defibrillator paddle is placed in covering contact over said upper sheet member said uncovered portion of said upper surface of said bottom sheet member will contact said electrode plate and be adhered thereto by means of said tacky characteristic of said conductive polymer;
    said upper sheet member being sized smaller than said bottom sheet member and said electrode plate of said defibrillator paddle, said uncovered portion of said upper surface of said bottom sheet member comprising at least an exposed strip extending around the perimeter of said upper sheet member.

8. A defibrillator pad according to claim 7 wherein said upper sheet member includes at least one aperture therein and said uncovered portion of said upper surface of said bottom sheet member is exposed through said aperture and is capable of contracting and adhering to said electrode plate of said defibrillator paddle when said electrode plate is placed in covering contact over said upper sheet member.

9. A defibrillator paddle according to claim 8 wherein said upper sheet member includes a plurality of apertures therein, said uncovered portion of said upper surface of said bottom sheet member being exposed through said plurality of apertures for contacting and adhering to said electrode plate when said electrode plate is placed in covering relation over said upper sheet member.

10. A defibrillator paddle according to claim 7 wherein said upper sheet member is comprised of metal foil.

11. In combination:
a bottom sheet member having a lower surface for engaging an adhering to a patient's chest and an upper surface, said bottom sheet member being comprised of a conductive polymer having a tacky characteristic so as to adhere to and form electrical contact with most surfaces it contacts;

an upper sheet member comprised of electrically conductive material and having an upper surface and a lower surface;
said lower surface of said upper sheet member being in contact with and covering a first portion of said upper surface of said bottom sheet member and being adhered thereto by means of said tacky characteristic of said conductive polymer;
said upper sheet member being shaped to expose at least one uncovered portion of said upper surface of said bottom sheet member;
a defibrillator paddle having an electrode plate, said electrode plate being in facing contact with said upper sheet member and with said uncovered portion of said bottom sheet member whereby said tacky characteristic of said bottom sheet member causes said uncovered portion thereof to detachably adhere to said electrode plate.

* * * * *